United States Patent

Nanba et al.

Patent Number: 5,286,476
Date of Patent: Feb. 15, 1994

[54] HAIR COSMETIC COMPOSITION

[75] Inventors: Tomiyuki Nanba; Kenji Torii; Hiroaki Yasuhara; Kenichi Tomita; Yoko Fukuchi, all of Yokohama, Japan

[73] Assignee: Shiseido Company Ltd., Tokyo, Japan

[21] Appl. No.: 708,095

[22] Filed: May 24, 1991

Related U.S. Application Data

[63] Continuation of Ser. No. 341,093, Apr. 20, 1989, abandoned, which is a continuation-in-part of Ser. No. 174,657, Mar. 29, 1988, abandoned.

[30] Foreign Application Priority Data

| Mar. 30, 1987 | [JP] | Japan | 62-77047 |
| Mar. 30, 1987 | [JP] | Japan | 62-77048 |
| Jul. 1, 1987 | [JP] | Japan | 62-164936 |
| Apr. 22, 1988 | [JP] | Japan | 63-99662 |

[51] Int. Cl.$^5$ .............................. A61K 7/00
[52] U.S. Cl. .................. 424/47; 424/70; 424/71; 424/63
[58] Field of Search .......... 424/70, 47, 71, 78, 424/63; A61K 7/06, 7/07, 7/075, 7/08

[56] References Cited

U.S. PATENT DOCUMENTS

| 4,336,246 | 6/1982 | Leon-Pekarek | 424/63 |
| 4,472,375 | 9/1984 | Bolich et al. | 424/70 |
| 4,515,784 | 5/1985 | Bogardus et al. | 514/859 |
| 4,704,272 | 11/1987 | Oh et al. | 514/938 X |
| 4,728,457 | 3/1988 | Fieler et al. | 252/DIG. 13 |
| 4,741,855 | 5/1988 | Grote | 252/312 X |
| 4,764,363 | 8/1988 | Bolich | 424/47 |
| 4,788,006 | 11/1988 | Bolich, Jr. et al. | 252/DIG. 13 |
| 4,834,968 | 5/1989 | Bolich, Jr. | 424/47 |
| 4,902,499 | 2/1990 | Bolich, Jr. et al. | 424/71 X |

FOREIGN PATENT DOCUMENTS

| 0155806 | 9/1985 | European Pat. Off. | A61K 7/075 |
| 63-313714 | 4/1989 | Japan. | |
| 2170216 | 7/1986 | United Kingdom | 424/70 |
| 2192194 | 1/1988 | United Kingdom | A61K 7/075 |

Primary Examiner—Paul R. Michl
Assistant Examiner—William E. Benston, Jr.
Attorney, Agent, or Firm—Sprung Horn Kramer & Woods

[57] ABSTRACT

A hair cosmetic composition contains one or more high molecular weight silicone compounds having the formula (I):

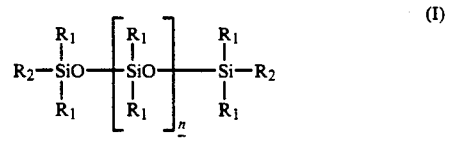

wherein $R_1$ represents a methyl group or a part thereof represents a phenyl group, $R_2$ represents a methyl or hydroxy group, and n represents an integer of 3,000 to 20,000.

10 Claims, No Drawings

HAIR COSMETIC COMPOSITION

CROSS-REFERENCE TO RELATED APPLICATION

This application is a continuation of application Ser. No. 341,093, filed Apr. 20, 1989, abandoned, which is a continuation-in-part of Ser. No. 174,657, filed Mar. 29, 1988, now abandoned.

BACKGROUND OF THE INVENTION

1. Field of the Invention

The present invention relates to a hair cosmetic composition giving an excellent luster to the hair, having a good set retentive force, imparting a smooth feeling to the hair, and having an excellent effect of preventing the generation of split hair and torn hair, and of repairing split hair.

2. Description of the Related Art

Generally speaking, when complicated hair treatments involving hair washing, brushing, heat from a dryer, hair coloring, and bleaching agents, etc. are applied repeatedly to the hair, the hair will be extensively damaged and the condition thereof deteriorated and, consequently, will become dry and unkempt, or an increased splitting of hair or of torn hair and a lowering in the strength of the hair occur, as is well known in the art.

Accordingly, to alleviate the hair damage as described above, to protect and repair hair, and to give a luster and smoothness to the hair, oil components such as silicone oil, ester oil, and hydrocarbon oil; cationic surfactants such as alkylammonium chloride; and a hair reinforcing agent such as a keratin decomposed product; have been formulated in hair cosmetics. Particularly, silicone oil having a degree of polymerization of 3 to 650 has a low surface tension and an excellent compatibility with hair, and gives a good luster thereto, and therefore, is now frequently used. The use of the oil component is limited, however, since if used in a large amount or over a long period, a drawback arises in that the hair becomes greasy. Also cationic surfactants are frequently used for imparting smoothness to the hair, but a desirable luster cannot be obtained thereby, and a drawback arises in that an absence of undesirable side effects cannot be guaranteed when these surfactants are formulated in a large amount.

Also, for setting hair, polymeric compounds, such as polyvinyl pyrrolidone type polymers, acidic polyvinyl ether type polymers, acidic acrylic polymers or cationic polymers, are employed, and although these compounds give an excellent fix, i.e., have a strong hair setting effect, they do not give a satisfactory luster and smoothness, and further, have a drawback of hardening i.e., stiffening, the hair.

Starting materials extracted from natural products have had some effect in hair damage prevention and protection from chemical or mechanical treatments, but none are satisfactory because, for example, the adhesiveness to the hair is weak or a feeling such as smoothness after use is unsatisfactory.

Furthermore, the conventional hair cosmetics do not provide a satisfactory prevention and restoration of split hair and torn hair, and split hair and torn hair are still the greatest causes of concern among women.

SUMMARY OF THE INVENTION

Accordingly, the objects of the present invention are to eliminate the above-mentioned disadvantages of the prior art and to provide a hair cosmetic composition which gives an excellent luster, imparts a smooth feeling to the hair without greasiness and stiffness, can prevent the generation of split hair or torn hair, and can repair such hair.

Other objects and advantages of the present invention will be apparent from the following description.

In accordance with the present invention, there is provided a hair cosmetic composition comprising at least one high molecular weight silicone having the formula (I):

$$R_2-\underset{\underset{R_1}{|}}{\overset{\overset{R_1}{|}}{Si}}O-\left[\underset{\underset{R_1}{|}}{\overset{\overset{R_1}{|}}{Si}}O\right]_n-\underset{\underset{R_1}{|}}{\overset{\overset{R_1}{|}}{Si}}-R_2 \quad (I)$$

wherein $R_1$ represents a methyl group or a part thereof represents a phenyl group, $R_2$ represents a methyl or hydroxyl group, and n represents an integer of 3000 to 20000.

In accordance with the present invention, there are also provided various hair cosmetic compositions containing, as an essential component, the above-mentioned high molecular weight silicone (I) and other components, as follows;

(A) 0.1% to 25% by weight of the above-mentioned high molecular weight silicone (I);
(B) 1% to 98.9% by weight of at least one cyclic silicone; and
(C) 1% to 98.9% by weight of trichlorotrifluoroethane and/or tetrachlorodifluoroethane.

(A) 0.1% to 25% by weight of the above-mentioned high molecular weight silicone (I);
(B) 45% to 98.9% by weight of at least one cyclic silicone; and
(C) 1% to 30% by weight of at least one lower alcohol.

(A) 0.01 to 25% by weight of the above-mentioned high molecular weight silicone (I);
(B) 1% to 98.9% by weight of trichlorotrifluoroethane and/or tetrachlorodifluoroethane; and
(C) 5% to 95% by weight of an aerosol propellant.

In accordance with the present invention there is further provided a preventive and restorative agent for split hair and torn hair comprising (A) 0.1% to 50% by weight of at least one high molecular weight silicone represented by the above-mentioned formula (I); and
(B) 1% to 99.9% by weight of a light fluid isoparaffin having 7 to 20 carbon atoms.

DESCRIPTION OF THE PREFERRED EMBODIMENT

The high molecular weight silicone (I) usable in the present invention has a high molecular weight and the value of n in the formula (I) is 3,000 to 20,000. The molecular weight is about 250,000 to 1,500,000, and soft rubbery properties are exhibited at normal temperatures.

Typical examples of this silicone are dimethylpolysiloxane, methylphenylpolysiloxane, dimethylpolysiloxane containing terminal hydroxyl groups, and methylphenylpolysiloxane containing terminal hydroxyl groups.

In the prior art, although dimethylpolysiloxanes having degrees of polymerization ranging from 3 to 650 have been used as the oil component in, for example, cosmetic compositions, there are no examples disclosed in which a high molecular weight silicone oil as in the present invention is formulated in such cosmetic compositions. The present cosmetic prevents and repairs damage such as split hair and torn hair by coating the damaged portion of the hair surface with a thin film of a high molecular weight silicone.

The amount of the high molecular weight silicone formulated may be 0.1% to 50% by weight, preferably 1% to 30% by weight, in the total amount of the cosmetic composition. When the amount is less than 0.1% by weight, a satisfactory effect will not be obtained, and when the amount exceeds 50% by weight, solubility is achieved only with difficulty.

The high molecular weight silicone of the present invention is formulated in a hair cosmetic composition, preferably by dissolving in a volatile or a low boiling point oil, or may be formulated separately into the hair cosmetic compositions and dissolved in the system.

Examples of the low boiling-point oil include low boiling-point linear silicones, low boiling-point cyclic silicones, and low boiling-point isoparaffinic hydrocarbons.

The low boiling-point linear silicone is represented by the formula (II) shown below, and specific examples thereof include hexamethyldisiloxane, octamethyltrisiloxane, decamethyltetrasiloxane, hexadecamethylheptasiloxane and the like.

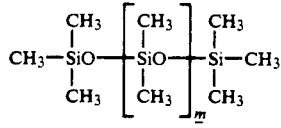

(II)

wherein m represents an integer of 0 to 5.

The low boiling-point cyclic silicone is represented by the formula (III) shown below, and specific examples thereof include octamethylcyclotetrasiloxane, decamethylcyclopentasiloxane, tetradecamethylcyclohexasiloxane and the like.

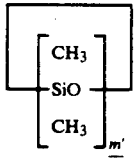

(III)

wherein m' represents an integer of 3 to 7.

The low boiling-point isoparaffinic hydrocarbon may include isoparaffinic hydrocarbons with boiling points at normal pressure of from 60° C. to 260° C., as exemplified by Isopar (trademark) A, C, D, E, G, H, K, L, M produced by Exxon Co., Shellsol 71 (trademark) produced by Shell Co., Soltol (trademark) 100, 130, or 220 produced by Phillips Co.

The above-mentioned low boiling-point oil may be used alone or in any mixture thereof, and the total amount formulated is preferably 1 to 50-fold by weight relative to the high molecular weight silicone, preferably 10% to 80% by weight, in the total weight of the hair cosmetic composition.

Any desired form of agent may be used in the present invention, and any of the solubilized system, the emulsified system, the powder dispersion system, the two layer oil-water system, and the three layer oil-water-powder system may be used.

In the emulsified system, generally the oil phase containing the high molecular weight silicone is emulsified with a nonionic surfactant, a cationic surfactant, an anionic surfactant or a mixture thereof. In this case, preferably the method is used in which a mixture of surfactants with a water-soluble polyhydric alcohol is previously prepared and then mixed with the oil phase, to obtain an emulsifier composition.

The water-soluble polyhydric alcohols usable in the present invention are polyhydric alcohols having two or more hydroxyl groups in the molecule. Typical examples of such polyhydric alcohols are dihydric alcohols such as ethylene glycol propylene glycol, trimethylene glycol, 1,2-butylene glycol, 1,3-butylene glycol, 1,4-butylene glycol, tetramethylene glycol, 2,3-butylene glycol, pentamethylene glycol 2-butene-1,4-diol, hexylene glycol, octylene glycol; trihydric alcohols such as glycerine, trimethylol propane, 1,2,6-hexanetriol and the like; tetrahydric alcohols such as penthaerythritol; pentahydric alcohols such as xylytol, etc.; hexahydric alcohols such as sorbitol, mannitol; polyhydric alcohol polymers such as diethylene glycol, dipropylene glycol, polyethylene glycol, polypropylene glycol, tetraethylene glycol, diglycerine, polyethylene glycol, triglycerine, tetraglycerine, polyglycerine; dihydric alcohol alkyl ethers such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether; dihydric alcohol alkyl ethers such as diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, dipropylene glycol butyl ether; dihydric alcohol ether esters such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate; glycerine monoalkyl ethers such as xyl alcohol, selachyl alcohol, batyl alcohol; sugar alcohols such as sorbitol, maltitol, maltotriose, mannitol, sucrose, erythritol, glucose, fructose, starch sugar, maltose, xylytose, starch sugar reduced alcohol, glysolid, tetrahydrofurfuryl alcohol, POE tetrahydrofurfuryl alcohol, POP butyl ether, POP POE butyl ether, tripolyoxypropylene glycerine ether, POP glycerine ether, POP glycerine ether phosphoric acid, POP POE pentanerythritol ether. These polyhydric alcohols, which may be used alone or in any mixture thereof, may be selected and used as desired.

As the oil constituting the oil phase of the emulsified cosmetic, other than the high molecular weight silicone according to the present invention, the following oils may be used.

Namely, oil components generally employed in cosmetics compositions including liquid oils and fats such as avocado oil, tsubaki oil, turtle oil, Macademia nuts oil, corn oil, mink oil, olive oil, rape seed oil, yolk oil, sesame oil, parsic oil, wheat germ oil, sasanqua oil, castor oil, linseed oil, safflower oil, cotton seed oil, perilla oil, soybean oil, peanut oil, tea seed oil, kaya oil, rice bran oil, Chinese tung oil, Japanese tung oil, hohoba oil, germ oil, triglycerine, trioctanoic acid glycerine, triisopalmitic acid glycerine; solid fats such as cacao fat, coconut oil, horse fat, hardened coconut fat, palm oil, tallow, sheep fat, hardened tallow, palm kernel oil, lard, ox bone fat, wood wax kernel oil, hardened castor oil; waxes such as beeswax, canderilla wax, cotton wax, carunauba wax, bayberry wax, insect wax, whale wax, montan wax, rice bran wax, lanolin, kapok wax, lanolin acetate, liquid lanolin, cane wax, isopropyl lanolin fatty acid, hexyllaurate, reduced lanolin, jojoba wax, hard lanolin, shellac wax, POE lanolin alcohol ether, POE lanolin alcohol acetate, POE cholesterol ether, lanolin fatty acid polyethylene glycol, POE hydrogenated lanolin alcohol ether; hydrocarbons such as fluid paraffin, ozocerite, squalene, pristan, paraffin, ceresin, squalane, petrolatum, microcrystalline wax; fatty acid oils, alcohols, ester oils such as cetyl octanoate, isopropyl myristate; silicone oils such as dimethylpolysiloxane, methylphenylpolysiloxane; silicone resins and the like.

The preferable formulated amounts of the above components are 0.5% to 10% by weight in the total amount of the hair cosmetic for the surfactant, and 10% to 80% by weight for the oil phase containing the high molecular weight silicone, and in the method of previously preparing a mixture of the surfactant and water-soluble polyhydric alcohol and mixing the mixture with the oil phase to give an emulsified composition, the surfactant is 1% to 20% by weight, the oil phase containing the high molecular weight silicone is 10% to 70% by weight, and the water-soluble polyhydric alcohol is preferably 5% to 30% by weight in the total amount of the hair cosmetic, and about 50% to 99% by weight based on the surfactant.

The emulsification form of the emulsified cosmetic can be the water-in-oil form or oil-in-water form, but is desirably prepared so that the water repellency effect of the present invention is not lost.

According to the second embodiment of the present invention, the hair cosmetic composition contains (A) 0.1% to 25% by weight, preferably 0.5% to 15% by weight, in view of the viscosity of the composition, of the above-mentioned high molecular weight silicone (I); (B) 1% to 98.9% by weight of the above-mentioned cyclic silicone; and (C) 1% to 98.9% by weight, preferably 1% to 50% by weight, of trichlorotrifluoroethane and/or tetrachlorodifluoroethane in the total composition, and optionally, lower alcohols such as ethanol and isopropyl alcohol are provided.

From the viewpoint of application of the present hair cosmetic compositions to the hair, the viscosity thereof is generally less than 30000 cps, preferably 20 to 5000 cps.

According to the third embodiment of the present invention, the hair cosmetic composition contains (A) 0.1% to 25% by weight, preferably 0.5 to 15% by weight, in view of the viscosity of the composition, of the above-mentioned high molecular weight silicone (I); (B) 45% to 98.9% by weight of the above-mentioned cyclic silicone; and (C) 1% to 30% by weight, preferably 5% to 15% by weight, of the lower alcohol such as ethanol, isopropyl alcohol.

From the viewpoint of application of the present hair cosmetic compositions to the hair, the viscosity thereof is generally less than 30000, preferably 20 to 5000 cps. The use of too large an amount of the lower alcohol will not allow the dissolution of the high molecular weight silicone.

According to the fourth embodiment of the present invention, the aerosol type hair cosmetic composition contains (A) 0.01 to 25% by weight, preferably 0.5% to 5% by weight, in view of the applicability of the composition to the hair, of the high molecular weight silicone (I); (B) 1% to 98.9% by weight, preferably 1% to 50% by weight of trichlorotrifluoroethane and/or tetrachlorodifluoroethane; and (C) 5% to 95% by weight, preferably 10% to 80% by weight of an aerosol propellant such as trichlorofluoromethane, dichlorodifluoromethane, dichlorotetrafluoroethane, monochlorodifluoromethane, dimethylether, propane, isobutane and/or n-butane; and, optionally, (D) a lower alcohol such as ethanol or isopropyl alcohol.

According to the fifth embodiment of the present invention, the high molecular weight silicone is contained in an amount of 0.1% to 50% by weight, preferably about 1% to 30% by weight, of the total weight of the preventive and restorative agent for split hair and torn hair. When the amount of the high molecular weight silicone is less than 0.1%, the desired effects cannot be obtained, and with an amount in excess of 50%, it becomes difficult to uniformly coat split hair and torn hair with the preventive and restorative agent, and thus the desired preventive and restorative effects cannot be obtained.

As the light fluid isoparaffin having 7 to 20 carbon atoms and usable in the present invention, there can be included isoparaffinic hydrocarbons having boiling points at normal pressure of within 90° to 260° C., including, for example, Isopar (trade mark) C, D, E, G, H, K, L, M, manufactured by Exon, Shellsol (trade mark) 71 manufactured by Shell, Soltrol (trade mark) 100, 130, 22 manufactured by Phillips, Nisseki Isosol (trade mark) 300, 400 manufactured by Nippon Sekiyu Kagaku, Permethyl 99A, 101A manufactured by Permethyl. Among the above, any desired one or more kinds of isoparaffins may be used, and the amount thereof is preferably 1 to 100-fold by weight relative to the high molecular weight silicone, more preferably 1% to 99.9% by weight, of the total amount of the preventive and restorative agent for split hair and torn hair.

In the preventive and restorative agent of the present invention, in addition to the above essential constituents, various components conventionally used for hair cosmetics can be formulated, depending on the purpose, within quantitative and qualitative ranges which do not impair the effect of the present invention. Examples of such components are oils such as avocado oil, palm oil, peanut oil, tallow, rice bran oil, jojoba oil, carunauba wax, lanolin, fluid paraffin, oxystearic acid, isostearyl palmitate, isostearyl alcohol; polyhydric alcohols such as ethylene glycol, propylene glycol, 1,3-butylene glycol, glycerine, sorbitol, polyethylene glycol; humectants such as hyaluronic acid, chondroitin sulfuric acid, pyrrolidone carboxylate; UV-ray absorbers or scattering agents such as amyl p-dimethylaminobenzoate, urocanic acid, ethyl diisopropylcinnamate, fine particulate titanium oxide, fine particulate zinc oxide, and lipophilic treated products or composite powders thereof; antioxidants such as sodium erysorbate, sage extract, vitamin E, p-hydroxyanisole; resins such as acrylic resin, silicon type resin, polyvinylpyrrolidone; protein or protein decomposed product such as soybean protein, gelatin, collagen, silk fibroin, elastin; preservatives such as ethyl paraben, butyl paraben; various amino acids; activators such as biotin, pantothenic acid; circulation promotors such as $\gamma$-oryzanol, sodium dextransulfate, vitamin E derivative; antiseborrheics such as sulfur, thianthol; diluents such as ethanol, isopropanol, tetrachlorodifluoroethane; surfactants; perfumes; water; thickeners such as carboxyvinyl polymer; colorants; and others.

The form of preparation of the present invention may be as desired, and may be one of, for example, a solubilized system, emulsified system, two-layer system of oil and water, and three-layer system of oil and water and powder.

In the case of the emulsified system, an oil phase containing a high molecular weight silicone is emulsified with a nonionic surfactant, a cationic surfactant, and an anionic surfactant, or a mixture thereof, to be used, but in this case, it is preferable to previously prepare a mixture of a surfactant and a water-soluble polyhydric alcohol, and then mix the mixture with the oil phase to form an emulsified composition.

In the hair cosmetic composition of the present invention, in addition to the above-mentioned essential constituents, UV-ray absorbers, anti-oxidants, preservatives, pharmaceutically active substances such as vitamins, hormones, and flavors may be formulated, depending on the purpose, within quantitative and qualitative ranges that will not impair the effect of the present invention.

EXAMPLES

The present invention will now be further illustrated by, but is by no means limited to, the following Examples and Comparative Examples, wherein all percentages are expressed on a weight basis unless otherwise noted.

EXAMPLE 1

| Hair Oil | |
|---|---|
| (1) Decamethylcyclopentasiloxane | 70.0% |
| (2) Dimethylpolysiloxane 5 cps | 20.0 |
| (3) Dimethylpolysiloxane ($R_1$ and $R_2$ in the formula (I) are a methyl group and n = 7000) | 10.0 |
| (4) Flavor | q.s. |

(1)–(4) were dissolved and mixed while stirring at 70°–80° C., and a viscous liquid hair oil with a viscosity of 500 cps and a good transparency was obtained.

EXAMPLE 2

| Hair Blow | |
|---|---|
| (1) Decamethylcyclopentasiloxane | 10.0% |
| (2) Methylphenylpolysiloxane (10% of $R_1$ in the formula (I) is a phenyl group and the remainder is a methyl group, $R_2$ is a methyl group and n = 15000) | 1.0 |
| (3) 1,3-Butylene glycol | 2.0 |
| (4) Polyethylene (60) hardened castor oil ester | 2.0 |
| (5) Ethyl alcohol 95% | 15.0% |
| (6) Purified water | 70.0% |
| (7) Flavor | q.s. |

(4) was dissolved in (3), emulsified by an addition of (1) and (2), and mixed with (5), (6), and (7). The composition was filled in a dispenser vessel, and sprayed in the atomized state onto the hair.

EXAMPLE 3

| Foamy Hair Setting Agent | |
|---|---|
| (1) Dimethylpolysiloxane 1.5 cps | 3.0% |
| (2) Dimethylpolysiloxane 20.0 cps | 2.0 |
| (3) Dimethylpolysiloxane ($R_1$ in the formula (I) is a methyl group, $R_2$ is a hydroxy group, and n = 5000) | 5.0 |
| (4) Glycerine | 3.0 |
| (5) Polyethylene glycol (120) hardened castor oil ester | 3.0 |
| (6) Behenyltrimethylammonium chloride | 0.7 |
| (7) Flavor | q.s |
| (8) Purified Water | 83.3 |

(4) and (5) were dissolved and then emulsified by an addition of a mixture of (1), (2), and (3), and the emulsified product thus obtained was added to and mixed with a mixture of (6), (7), and (8).

EXAMPLE 4

| Hair Oil | |
|---|---|
| (1) Decamethylcyclopentasiloxane | 80.0% |
| (2) Dimethylpolysiloxane ($R_1$ and $R_2$ in the formula (I) are methyl groups and n = 4,000) | 8.0 |
| (3) Organic silicone resin comprising $(CH_3)_3SiO_\frac{1}{2}SiO_2/(CH_3)_2SiO = 2.4/1.6 = 1.0$ (molar ratio) | 2.0 |
| (4) Ethanol | 10.0 |
| (5) Flavor | q.s. |

(1) through (5) were dissolved while stirring at 70°–80° C. to obtain a liquid hair oil with a viscosity of 700 cps.

EXAMPLE 5

| Hair Oil | |
|---|---|
| (1) Decamethylcyclopentasiloxane | 40.0% |
| (2) Dimethylpolysiloxane ($R_1$ and $R_2$ in the formula (I) are a methyl group and n = 3000) | 10.0 |
| (3) Trichlorotrifluoroethane | 50.0 |

(1) through (3) were dissolved and mixed while stirring, and a viscous liquid hair oil with a viscosity of 200 cps and a good transparency was obtained.

EXAMPLE 6

| Hair Oil | |
|---|---|
| (1) Octamethylcyclotetrasiloxane | 20.0% |
| (2) Dimethylpolysiloxane | 0.5 |
| ($R_1$ in the formula (I) is a methyl group, $R_2$ a hydroxyl group, and n = 10000) | |
| (3) Trichlorotrifluoroethane | 79.5 |

A liquid hair oil with a viscosity of 8 cps was obtained in the same manner as in Example 6.

EXAMPLE 7

| Hair Oil | |
|---|---|
| (1) Dodecamethylcyclohexanesiloxane | 30.0% |
| (2) Dimethylpolysiloxane | 25.0 |
| (Methyl: Phenyl in $R_1$ in the formula (I) = 1:1, $R_2$ is methyl, and n = 20000) | |
| (3) Isopropyl alcohol | 5.0 |
| (4) Trichlorotrifluoroethane | 20.0 |
| (5) Tetrachlorodifluoroethane | 20.0 |

A transparent liquid hair oil with a viscosity of 2000 cps was obtained in the same manner as in Example 6.

EXAMPLE 8

| Hair Oil | |
|---|---|
| (1) Decamethylcyclopentanesiloxane | 20.0% |
| (2) Octamethylcyclotetrasiloxane | 20.0 |
| (3) Ethanol (95%) | 25.0 |
| (4) Tetrachlorodifluoroethane | 20.0 |
| (5) Dimethylpolysiloxane | 15.0 |

($R_1$ and $R_2$ in the formula (I) are methyl group and n=15,000)

A transparent liquid hair oil with a viscosity of 1500 cps was obtained in the same manner as in Example 6.

EXAMPLE 9

| Hair Oil | |
|---|---|
| (1) Decamethylcyclopentasiloxane | 70.0% |
| (2) Ethanol | 20.0 |
| (3) Dimethylpolysiloxane | 10.0 |
| ($R_1$ and $R_2$ in the formula (I) are a methyl group and n = 3000) | |
| (4) Flavor | q.s. |

(1) through (4) were dissolved and mixed while stirring, and a viscous liquid hair oil with a viscosity of 500 cps and a good transparency was obtained.

EXAMPLE 10

| Hair Oil | |
|---|---|
| (1) Octamethylcyclotetrasiloxane | 69.9% |
| (2) Dimethylpolysiloxane | 0.1 |
| ($R_1$ in the formula (I) is a methyl group, $R_2$ a hydroxyl group, and n = 10000) | |
| (3) Ethanol (99%) | 30.0 |

A liquid hair oil with a viscosity of 20 cps was obtained in the same manner as in Example 9.

EXAMPLE 11

| Hair Oil | |
|---|---|
| (1) Dodecamethylcyclohexasiloxane | 45.0% |
| (2) Dimethylpolycyclohexane | 25.0 |
| (Methyl: Phenyl in $R_1$ in the formula (I) = 1:1, $R_2$ is a methyl group, and n = 20000) | |
| (3) Isopropylalcohol | 30.0 |
| (4) Flavor | q.s. |

A liquid hair oil with a viscosity of 5000 cps was obtained in the same manner as in Example 9.

EXAMPLE 12

| Hair Oil | |
|---|---|
| (1) Decamethylcyclopentasiloxane | 40.0% |
| (2) Octamethylcyclotetrasiloxane | 40.0 |
| (3) Dimethylpolysiloxane | 5.0 |
| ($R_1$ and $R_2$ are a methyl group and n = 5000) | |
| (4) Dimethylpolysiloxane | 10.0 |
| (Methyl: phenyl in $R_1$ of the formula (I) = 1:1, $R_2$ is hydroxyl, and n = 15000) | |
| (5) Ethanol (95%) | 2.0 |
| (6) Isopropylalcohol | 3.0 |

A transparent liquid hair oil with a viscosity of 2500 cps was obtained in the same manner as in Example 9.

EXAMPLE 13

| Hair Spray | |
|---|---|
| (1) Dimethylpolysiloxane | 0.5% |
| (Methyl: phenyl in the formula (I) = 1:1, $R_2$ is methyl, and n = 10000) | |
| (2) Trichlorotrifluoroethane | 50.0 |
| (3) Trichlorofluoromethane | 20.0 |
| (4) Dichlorodifluoromethane | 30.0 |

(1) and (2) were dissolved and mixed by stirring, and the resultant mixture was charged into an aerosol container. Then, after attaching a valve, (3) and (4) were added thereto.

EXAMPLE 14

| Hair Spray | |
|---|---|
| (1) Dimethylpolysiloxane | 2.5% |
| ($R_1$ and $R_2$ in the formula (I) are a methyl group and n = 3000) | |
| (2) Dimethylpolysiloxane | 2.5 |
| ($R_1$ is methyl, $R_2$ hydroxyl, and n = 20,000) | |
| (3) Tetrachlorodifluoroethane | 10.0 |
| (4) Trichlorotrifluoroethane | 5.0 |
| (5) Dodecamethylcyclohex siloxane | 5.0 |
| (6) Isoper | 10.0 |
| (7) Ethanol | 5.0 |
| (8) Flavor | q.s. |
| (9) Diethyl ether | 30 |
| (10) n-Butane | 30 |

(1) through (8) were dissolved and mixed by stirring, and the resultant mixture was charged into an aerosol container. Then, after attaching a valve, (9) and (10) were added thereto.

EXAMPLE 15

| Hair Spray | |
|---|---|
| (1) Dimethylpolysiloxane | 0.5% |
| ($R_1$ and $R_2$ in the formula (I) are methyl and n = 10,000) | |
| (2) Tetrachlorodifluoroethane | 2.0 |
| (3) Decamethylcyclopentasiloxane | 75.5 |
| (4) Ethanol | 2.0 |
| (5) Isopropylalcohol | 10.0 |
| (6) Flavor | q.s. |
| (7) Propane | 7.0 |
| (8) Dimethyl ether | 3.0 |

(1) through (6) were dissolved and mixed by stirring, and the resultant mixture was charged into an aerosol container. The after attaching a valve, (1) and (8) were added thereto.

The hair cosmetic compositions according to Examples 1 to 15 of the present invention gave an excellent luster and smoothness to the hair, and hair damage preventing and repairing effects, and had a strong hair setting effect.

EXAMPLE 16

| Hair Blow | |
|---|---|
| (1) Decamethylcyclopentasiloxane | 15% |
| (2) Dimethylpolysiloxane | 4 |
| ($R_1$ and $R_2$ in the formula (I) are methyl groups and n = 3000) | |
| (3) 1,3-butylene glycol | 2 |
| (4) Polyethylene (60) hardened castor oil ester | 2 |
| (5) Ethanol | 15 |
| (6) Deionized water | 62 |
| (7) Flavor | q.s. |

(2) was dissolved in (1), the resultant solution was added to a mixture of (3) and (4) to be emulsified, and the emulsion then mixed with (5), (6), and (7).

EXAMPLE 17

| Hair Mousse (Trademark) | |
|---|---|
| (1) Octamethylcyclotetrasiloxane | 13% |
| (2) Dimethylpolysiloxane | 2 |
| ($R_1$ and $R_2$ are methyl groups and n = 10000) | |
| (3) Glycerol | 1 |
| (4) Polyethylene (120) hardened castor oil ester | 2 |
| (5) Ethanol | 10 |
| (6) Deionized water | 62 |
| (7) N-butane | 7 |
| (8) Flavor | q.s. |

(2) was dissolved in (1), the resultant solution was added to a mixture of (3) and (4) to be emulsified, and the emulsion then mixed with (5), (6), and (7). This mixture was charged into an aerosol container, and after attaching a valve, (8) was filled therein.

EXAMPLE 18

| Hair Cream | |
|---|---|
| (1) Decamethylcyclohexasiloxane | 28% |
| (2) Dimethylpolysiloxane | 6 |
| ($R_1$ and $R_2$ in the formula (I) are methyl groups and n = 10000) | |
| (3) Glycerol | 3 |
| (4) Polyethylene (120) hardened castor oil ester | 3 |
| (5) Ethanol | 10 |

-continued

| Hair Cream | |
|---|---|
| (6) Deionized water | 57 |
| (7) Polyvinyl alcohol | 1 |
| (8) Flavor | q.s. |

(2) was dissolved in (1), the resultant solution was added to a mixture of (3) and (4) to be emulsified, and the emulsion was mixed with (5), (6), (7), and (8).

EXAMPLE 19

| Liquid Preventive and Restorative Agent | |
|---|---|
| (1) Decamethylcyclopentasiloxane | 60.0% |
| (2) Dimethylpolysiloxane (5 cps) | 20.0 |
| (3) Dimethylpolysiloxane | 10.0 |
| ($R_1$ and $R_2$ in the formula (I) are methyl groups and n = 7000) | |
| (4) Ethanol | 10 |
| (5) Flavor | q.s. |

(1) through (5) were dissolved and mixed by stirring at 70° to 80° C., and a viscous liquid hair oil with a viscosity of 500 cps and a good transparency was obtained.

COMPARATIVE EXAMPLE 1

| Hair Oil | |
|---|---|
| (1) Decamethylcyclopentasiloxane | 60.0% |
| (2) Dimethylpolysiloxane (5 cps) | 30.0 |
| (3) Ethanol | 10 |
| (4) Flavor | q.s. |

(1) through (4) were dissolved and mixed by stirring at 70° to 80° C., and a viscous liquid hair oil with a viscosity of 500 cps and a good transparency was obtained.

COMPARATIVE EXAMPLE 2

| Liquid Hair Conditioner | |
|---|---|
| (1) Vinylpyrrolidone/vinyl acetate copolymer | 2.0% |
| (2) Propylene glycol | 2.0 |
| (3) Ethanol | 40.0 |
| (4) Deionized water | 56.0 |

After (1) was dissolved in (3), the thus-obtained solution was added to (2) and (4) to obtain a transparent liquid hair conditioner.

EVALUATION TEST

The properties and effects of the products of the present invention obtained in Examples 16 through 19 and the conventional products obtained in Comparative Examples 1 and 2 as described above are shown below.

1. The split hair generation preventive effect was evaluated. Bundles of hair collected from the same person were prepared, the samples were respectively applied to each bundle, and the number of split hairs generated by a mechanical brushing of 10000 strokes was counted.

| Sample | Number of split hairs generated |
|---|---|
| Example 17 | 100/1300 |
| Example 19 | 30/1300 |

| Sample | Number of split hairs generated |
| --- | --- |
| Comparative Example 1 | 200/1300 |
| Uncoated | 300/1300 |

The products of the present invention exhibited a remarkable split hair generation prevention effect.

2. The effect of split hair generation prevention in actual use was evaluated. A panel of six members was requested to use the hair oil of Example 19 on one half of the hair on the head and a sample of Comparative Example 1 on the other half, every day, and the amounts of split hairs generated on the corresponding sides after two months were compared.

| Panel No. | Example 19 | Comparative Example 1 |
| --- | --- | --- |
| A | ± | − |
| B | + | − |
| C | + | ± |
| D | + + | ± |
| E | + + | ± |
| F | + + | ± |

++ Very few
+ Few
± Some
− Many

It was found that the generation of split hair was reduced in the hair on which the product of the present invention was applied.

3. The split hair repairing effect was determined. Example 16 was used on the hair of panel members having many split hairs, and the effect of preventing a splitting of the hairs was observed.

| Panel No. | Conspicuous hair splitting |
| --- | --- |
| G | + |
| H | + |
| I | + + |
| J | + + |

++ Not conspicuous
+ Slightly conspicuous

It was found that the use of the product of the present invention substantially prevented hair splitting.

4. The smoothness was evaluated by a friction measuring machine, and the reduction of the frictional coefficient of the hair was determined.

| Sample | Frictional coefficient |
| --- | --- |
| Example 17 | 0.25 |
| Example 19 | 0.2 |
| Comparative Example 1 | 0.35 |
| Comparative Example 2 | 0.6 |
| Uncoated | 0.5 |

The smaller frictional coefficient represented a greater smoothness, and as can be seen, hair became smoother when the product of the present invention was used.

EXAMPLE 20

| Liquid Preventive and Restorative Agent | |
| --- | --- |
| (1) Light fluid isoparaffin ($C_{11-12}$) | 90.0% |
| (2) Dimethylpolysiloxane ($R_1$ and $R_2$ are methyl groups and n = 7000) | 10.0 |
| (3) Perfume | q.s. |

The components (1) through (3) were dissolved and mixed by stirring to obtain a viscous liquid preventive and restorative agent with a good transparency and having a viscosity of 600 cps.

EXAMPLE 21

| Aerosol Type Preventive and Restorative Agent | |
| --- | --- |
| (1) Light fluid isoparaffin ($C_{12-15}$) | 22.0% |
| (2) Dimethylpolysiloxane ($R_1$ and $R_2$ are methyl groups and n = 20000) | 3.0 |
| (3) Propylene glycol | 6.0 |
| (4) Polyoxyethylene (80 mol) hardened castor oil ester | 2.0 |
| (5) Cationized cellulose Polymer JR-400 (manufactured by UCC) | 0.2 |
| (6) Water-soluble elastin | 10.0 |
| (7) Deionized water | 47.8 |
| (8) Dimethyl ether | 4.0 |
| (9) Dichlorodifluoromethane | 6.0 |

To the mixture of (3) and (4) was added a mixed and dissolved product of (1) and (2), followed by emulsification. To the resultant emulsion was added the solution of (5) through (7), and the mixture was mixed and stirred to obtain a stock liquor. The stock liquor was filled in an aerosol can, and subsequently, the propellant gases of (8) and (9) were filled to obtain an aerosol type preventive and restorative agent.

COMPARATIVE EXAMPLE 3

| Liquid Hair Oil | |
| --- | --- |
| (1) Light fluid isoparaffin ($C_{12-15}$) | 60.0% |
| (2) Dimethylpolysiloxane (5 cps) | 30.0 |
| (3) Ethanol | 10.0 |
| (4) Perfume | q.s. |

The components (1) through (4) were mixed to obtain a liquid hair oil.

COMPARATIVE EXAMPLE 4

| Liquid Hair Cosmetic | |
| --- | --- |
| (1) Vinyl pyrrolidone/vinyl acetate copolymer | 2.0% |
| (2) Propylene glycol | 2.0 |
| (3) Ethanol | 40.0 |
| (4) Deionized water | balance |

The components (1) through (4) were dissolved to obtain a liquid hair cosmetic.

For Examples 20 and 21 and Comparative Examples 3 and 4, the split hair generation preventive effect, the split hair restorative effect, and smoothness of the hair were measured.

TEST EXAMPLE 1

Measurement of Split Hair Generation Preventive Effect

Hair bundles were prepared from the hair collected from the same person, and each hair bundle was coated with the sample shown below, and the number of split hairs generated when brushing was applied mechanically for 10,000 times was counted. Each hair bundle consisted of 1300 hairs.

| Sample | Number of Split Hair Generated |
| --- | --- |
| Example 20 | 30 |
| Example 21 | 100 |
| Comparative Example 3 | 200 |
| Uncoated | 300 |

As apparent from the above Table, the present product exhibited remarkable split hair generation preventive effect.

TEST EXAMPLE 2

Measurement of Split Hair Generation Preventive Effect in Actual Use

A panel of 6 members were asked to use the sample of Example 1 for half of the hair on the head and the sample of Comparative Example 1 for the remaining half, every day, and the amounts of split hair generated on the left and right halves after 2 months were compared.

Rating

++: less than 10% of split hair generation ratio
+: 10% to 15% of split hair generation ratio
±: 15% to 20% of split hair generation ratio
−: 20% or more of split hair generation

| Panel No. | Example 20 | Comparative Example 3 |
| --- | --- | --- |
| A | ± | − |
| B | + | − |
| C | + | ± |
| D | ++ | ± |
| E | ++ | ± |
| F | ++ | ± |

For all of the panel members, the hair on which the present product was employed showed a reduced generation of split hair, thereby confirming the split hair generation preventive effect of the present product.

TEST EXAMPLE 3

Measurement of Split Hair Restorative Effect

Four members of the panel with a large amount of split hair were asked to use the preventive and restorative agent of Example 20, for observation of the restorative effect of split hair.

As the result, for each member of the panel, the amount of split hair was reduced, thereby confirming the restorative effect of the present product.

TEST EXAMPLE 4

Measurement of Smoothness of Hair

The frictional coefficient of hair was measured by a friction measuring instrument.

| Sample | Frictional coefficient |
| --- | --- |
| Example 20 | 0.2 |
| Example 21 | 0.25 |
| Comparative Example 3 | 0.35 |
| Comparative Example 4 | 0.6 |
| Uncoated | 0.5 |

As shown above, with the present product the frictional coefficient was remarkably reduced.

EXAMPLE 22

| Liquid Preventive and Restorative Agent | |
| --- | --- |
| (1) Light fluid isoparaffin ($C_{16-19}$) | 30.0% |
| (2) Methylphenylpolysiloxane ($R_1$ is a methyl group: phenyl group = 1:1, $R_2$ is a methyl group, and n = 10000) | 5.0 |
| (3) Tetrachlorodifluoroethane | 54.0 |
| (4) Alkyl methacrylate, dimethylaminoethyl methacrylate copolymer amphoteric product | 1.0 |
| (5) Ethanol | 10.0 |

The components (1) through (5) were mixed and dissolved by stirring to obtain a viscous liquid preventive and restorative agent with a good transparency.

EXAMPLE 23

| Liquid Preventive and Restorative Agent | |
| --- | --- |
| (1) Light fluid isoparaffin ($C_{12-15}$) | 84.0% |
| (2) Dimethylpolysiloxane ($R_1$ is a methyl group, $R_2$ is a hydroxyl group, and n = 10000) | 1.0 |
| (3) Silicone resin with ($C_6H_5$)$SiO_{3/2}$ units: $(CH_3)_2SiO_2$ units = 5.67:1. | 5.0 |
| (4) Ethanol | 10.0 |
| (5) Perfume | q.s. |

The components (1) through (5) were dissolved by mixing and stirring to obtain a viscous liquid preventive and restorative agent with a good transparency.

EXAMPLE 24

| Liquid Preventive and Restorative Agent | |
| --- | --- |
| (1) Light fluid isoparaffin ($C_{8-9}$) | 54.3% |
| (2) Soltrol (trade mark) 130 | 45.0 |
| (3) Dimethylpolysiloxane ($R_1$ and $R_2$ are methyl groups, and n = 20000) | 0.1 |
| (4) Amino-modified silicon oil Silicon SM8702C (manufactured by Toray Silicon) | 0.1 |
| (5) Silicon polyether copolymer Silicon KF945(A) (manufactured by Toray Silicon) | 0.5 |

The components (1) through (5) were dissolved by mixing and stirring to obtain a viscous liquid preventive and restorative agent with a good transparency.

EXAMPLE 25

| Emulsion Preventive and Restorative Agent | |
| --- | --- |
| (1) Shellsol 71 (manufactured by Shell) | 15.0% |
| (2) Methylphenylpolysiloxane ($R_1$ is a methyl group: phenyl group = 1:1, $R_2$ is a methyl group, and n = 8000) | 3.0 |
| (3) 1,3-Butylene glycol | 2.0 |
| (4) Polyoxyethylene (60 mol) hardened castor oil ester | 2.0 |
| (5) Titanium oxide sol Neosunbale W-10 (manufactured by Shokubai Kasei Kogyo) | 10.0 |
| (6) Ethanol | 15.0 |
| (7) Deionized water | 53.0 |
| (8) Perfume | q.s. |

The component (1) was dissolved in (2), the solution was added to a mixture of (3) and (4) to be primarily emulsified, and then the components (5) through (8) were added to effect a reemulsification and obtain a preventive and restorative agent.

EXAMPLE 26

| Cream Preventive Restorative Agent | |
|---|---|
| (1) Isosol 300 (manufactured by Nippon Sekiyu Kagaku) | 10.0% |
| (2) Dimethylpolysiloxane ($R_1$ and $R_2$ are methyl groups and n = 5000) | 3.0 |
| (3) Dimethylpolysiloxane (20 cps) | 5.0 |
| (4) Glycerine tri-2-ethylhexanoate | 8.0 |
| (5) Petrolatum | 5.0 |
| (6) Stearyl alcohol | 2.0 |
| (7) Sorbitane monooleate | 2.0 |
| (8) Polyoxyethylene (40 mol) hardened castor oil ester | 2.0 |
| (9) Glycerine | 5.0 |
| (10) Hyaluronic acid | 5.0 |
| (11) Preservative | q.s. |
| (12) Deionized water | balance |

The components (1) through (8) were dissolved with stirring and added into a dissolved product of (9) through (12), to be emulsified and obtain a cream preventive and restorative agent.

EXAMPLE 27

| Liquid Preventive and Restorative Agent | |
|---|---|
| (1) Light fluid isoparaffin ($C_{12-15}$) | 40.0% |
| (2) Dimethylpolysiloxane ($R_1$ is a methyl group, $R_2$ is a hydroxyl group, and n = 5000) | 30.0 |
| (3) Tetrachlorodifluoroethane | 20.0 |
| (4) Ethanol | 9.9 |
| (5) 2,4-Methoxybenzophenone | 0.1 |
| (6) Perfume | q.s. |

The components (1) through (6) were dissolved by mixing and stirring to obtain a viscous liquid preventive and restorative agent with a good transparency.

EXAMPLE 28

| Spray Type Preventive and Restorative Agent | |
|---|---|
| (1) Decamethylcyclopentasilicone | 77.5% |
| (2) Dimethylpolysiloxane ($R_1$ and $R_2$ are methyl groups and n = 10000) | 0.5 |
| (3) Ethanol | 2.0 |
| (4) Isopropyl alcohol | 10.0 |
| (5) Perfume | q.s. |
| (6) Propane | 7.0 |
| (7) Dimethyl ether | 3.0 |

The components (1) through (5) were mixed and dissolved, the solution was filled in an aerosol can, and a valve was mounted thereon, followed by filling with the propellants (6) and (7) to obtain a spray type preventive and restorative agent.

EXAMPLE 29

| Liquid Preventive and Restorative Agent | |
|---|---|
| (1) Octamethyltrisiloxane | 5.0% |
| (2) Dimethylpolysiloxane ($R_1$ and $R_2$ are methyl groups and n = 10000) | 1.0 |
| (3) Trichlorotrifluoroethane | 93.9 |
| (4) 2-Ethylhexyl-p dimethylaminobenzoate | 0.1 |

The components (1) through (4) were dissolved by stirring to obtain a viscous liquid preventive and restorative agent with a good transparency.

The preventive and restorative agent for split hair and torn hair according to the present invention has an excellent effect of preventing the split hair and torn hair from which a majority of women suffer, and for restoring the split hair by coating the hair with the present product. Also, as a secondary effect, the present product gives the hair a smooth finish.

We claim:

1. A method of preventing generation of split hair or torn hair for restoring worn hair which comprises applying to the hair a hair cosmetic composition comprising (a) 0.1% to 50% by weight of at least one high molecular weight silicone having the formula (I):

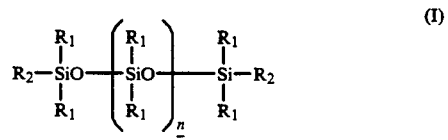

wherein $R^1$ represents a methyl group or a part thereof represents a phenyl group, $R^2$ represents a methyl or hydroxy group, and n represent an integer from 3000 to 20000; and (b) 1 to 50-fold by weight, relative to the high molecular weight silicone, of a low boiling-point oil having a boiling point of 60° C. to 260° C. at normal pressure.

2. A method as claimed in claim 1, wherein the hair cosmetic composition is an oil-in water emulsified cosmetic composition containing a nonionic, cationic, or anionic surfactant.

3. A method as claimed in claim 2, wherein the emulsified cosmetic composition is an emulsified cosmetic composition which is emulsified by mixing a mixture of a water-soluble polyhydric alcohol and a surfactant with an oil phase.

4. A method as claimed in claim 1, wherein said hair cosmetic composition comprises:

(A) 0.1% to 25% by weight of at least one high molecular weight silicone having the formula (I):

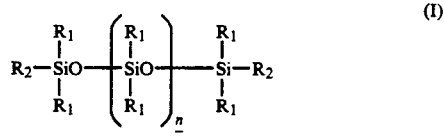

wherein $R_1$ represents a methyl group or a part thereof represents a phenyl group, $R_2$ represents a methyl or hydroxy group, and n represents integer from 3000 to 20000;

(B) 1% to 98.9% by weight of at least one cyclic silicone; and (C) 1% to 98.9% by weight of a component selected from the group consisting of trichlorotrifluoroethane, tetra-chlorodifluoroethane and mixtures thereof.

5. A method as claimed in claim 1, wherein said hair cosmetic composition comprises:

(A) 0.1% to 25% by weight of at least one high molecular weight silicone having the formula (I):

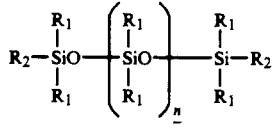

wherein

R$_1$ represents a methyl group or a part thereof represents a phenyl group,

R$_2$ represents a methyl or hydroxy group, and n represents an integer from 3000 to 20000;

(B) 45% to 98.9% by weight of at least one cyclic silicone; and (C) 1% to 30% by weight of at least one lower alcohol selected from the group consisting of ethanol, isopropyl alcohol and mixtures thereof.

6. A method as claimed in claim 1, wherein said hair cosmetic composition is an aerosol hair cosmetic composition comprising:

(A) 0.1% to 25% by weight of at least one high molecular weight silicone having the formula (I):

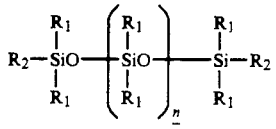

wherein

R$_1$ represents a methyl group or a part thereof represents a phenyl group,

R$_2$ represents a methyl or hydroxy group, and n represents an integer from 3000 to 20000;

(B) 1% to 98.9% by weight of a component selected from the group consisting of trichlorotrifluoroethane, tetrachlorodifluoroethane and mixtures thereof; and (C) 5% to 95% by weight of an aerosol propellant.

7. A method as claimed in claim 6, wherein the aerosol propellant is at least one compound selected from the group consisting of trichlorofluoromethane, dichlorodifluoromethane, dichlorotetrafluoroethane, monochlorodifluoromethane, dimethylether, propane, isobutane and n-butane.

8. A method as claimed in claim 1, wherein the low boiling-point oil is at least one member selected from the group consisting of dimethylpolysiloxane, octamethylcyclotetrasiloxane, decamethylcyclopentasiloxane, dodecamethylcyclohexasiloxane and an isoparaffinic hydrocarbon having 1 to 30 carbon atoms.

9. A method as claimed in claim 1, wherein said low boiling point oil is one of octamethylcyclotetrasiloxane, decamethylcyclopentasiloxane and dodecamethylcyclohexasiloxane.

10. A method as claimed in claim 1, wherein the low boiling-point oil is at least one member selected from the group consisting of hexamethyldisiloxane, octamethyltrisiloxane, decamethyltetrasiloxane and hexadecamethylheptasiloxane.

* * * * *